United States Patent

Boivin et al.

[11] Patent Number: 5,977,395
[45] Date of Patent: Nov. 2, 1999

[54] ESTER SYNTHESES AND TRANSESTERIFIABLE XANTHATE REACTANTS THEREFOR

[75] Inventors: Jean Boivin, Forges-les-Bains; Eric B. Henriet, Creteil; Samir Z. Zard, Gif-sur-Yvette, all of France

[73] Assignee: Rhone-Poulenc Chimie, Courbevoie Cedex, France

[21] Appl. No.: 08/819,938

[22] Filed: Mar. 18, 1997

Related U.S. Application Data

[62] Division of application No. 08/452,718, May 30, 1995, Pat. No. 5,637,722.

[30] Foreign Application Priority Data

May 27, 1994 [FR] France ..................... 94 06449

[51] Int. Cl.$^6$ .................................. C07C 329/16
[52] U.S. Cl. .................................. 558/243; 558/245
[58] Field of Search .................. 548/211; 558/243, 558/245

[56] References Cited

U.S. PATENT DOCUMENTS 3,522,221  7/1970  Gardiner et al. .

FOREIGN PATENT DOCUMENTS 0 442 077 A2  8/1991  European Pat. Off. .

OTHER PUBLICATIONS (Houben–Weyl). "Methoden der Organischen Chemie", 1955, pp. 817–819, Auflage, Band IX.

J. Boivin et al. "A Novel Synthesis of 1, 3–Dithiol–2–ones from S–Propargyl Dithiocarbonates", vol. 34, No. 17, Apr. 23, 1993, pp. 2763–2766, Tetrahedron Letters.

J. Boivin et al. "Novel Formal 3+2 Annulation Reaction Based on S–Propargyl Dithiocarbonates (Xanthates)", vol. 113, No. 21, Jul. 17, 1991, pp. 5874–5876, Journal of the American Chemical Society.

K. Harano et al. "A Simple One–Pot Synthesis of Hydroisobenzothiophenes Via Three–Step Sequential Pericyclic Reactions of Xanthates", vol. 32, No. 21, May 20, 1991, pp. 2387–2390, Tetrahedron Letters.

A. Le Minor et al. "Synthesis of S–Dithiocarbonates with Polymer–Supported Xanthates", vol. 21, No. 5, May 1989, pp. 445–448, Polymer Bulletin.

N. F. Haley et al. "Efficient and General Synthesis of 1,3–Dithiole–2–thiones", vol. 45, No. 1, Jan. 1980, pp. 175–177, Journal of Organic Chemistry.

M. I. Aliev et al. "Synthesis of Some Xanthates", vol. 70, No. 17, Apr. 28, 1969, Abstract No. 77272t, p. 276.

*Primary Examiner*—Robert W. Ramsuer
*Assistant Examiner*—Ebenezer Sackey
*Attorney, Agent, or Firm*—Burns, Doane, Swecker & Mathis, L.L.P.

[57] ABSTRACT

"Esters" are synthesized by reacting a nucleophile with a propargyl xanthate advantageously having the formula (I):

$$R_3-C\equiv C-CR_1R_2-S-CS-Y-R \qquad (I)$$

in the presence of at least one acid, Brönsted or otherwise, and at a temperature ranging from 0° to 300° C.; the subject reaction is particularly applicable to a wide variety of chiral organic syntheses.

2 Claims, No Drawings

ESTER SYNTHESES AND TRANSESTERIFIABLE XANTHATE REACTANTS THEREFOR

This application is a divisional of application Ser. No. 08/452,718, filed May 30, 1995 now U.S. Pat. No. 5,637,722.

BACKGROUND OF THE INVENTION

1. Technical Field of the Invention

The present invention relates to a novel process for the synthesis of esters, to the reactants therefor, and to a novel class of transesterifiable xanthates which comprise said reactants.

2. Description of the Prior Art

Nucleophilic substitution reactions are very widely used, but certain of which are very difficult to carry out; thus, novel leaving groups which are very reactive and easy to prepare are increasingly in demand.

Moreover, one of the most persistent problems in this art is to convert a hydroxyl-type function into a leaving group.

It too is preferable that the reaction be carried out such that the leaving group maintains the chirality of the radical to which it is bonded (whether by inverting or preserving same).

SUMMARY OF THE INVENTION

Accordingly, a major object of the present invention is the provision of unique leaving groups, which, upon leaving, maintain the chirality of the alkyl moiety (in the etymological sense) to which it was bonded.

Another object of the present invention is the provision of a process for the realization of such novel leaving groups.

Yet another object of this invention is the provision of a family of reactants for the alkylation of nucleophiles, even nucleophiles which are weak or difficult to react.

Still another object of the present invention is the provision of a family of reactants for the alkylation of acids, even acids which are poorly nucleophilic (pKa at most equal to 3, preferably equal to 1) or difficult to react (namely, sterically hindered).

Another object of this invention is the provision of a family of reactants for the alkylation of nucleophiles without racemization of the alkyl moiety.

Yet another object of the present invention is the provision of a family of reactants for the alkylation of nucleophiles with Walden inversion of the alkyl moiety.

Briefly, the present invention features a process for alkylating a nucleophile, comprising reacting said nucleophile with an alkyl propargyl xanthate in the presence of an acid at a temperature ranging from 0° to 300° C.

DETAILED DESCRIPTION OF BEST MODE AND PREFERRED EMBODIMENTS OF THE INVENTION

More particularly according to the present invention, the nucleophile reactant typically comprises a labile hydrogen atom. The presence of a labile hydrogen atom indicates that the nucleophile is capable of releasing a hydrogen ion after the first step of the alkylation.

In this event, it may be represented by the general formula:

H—(X)

in which X is the residue of an organic or inorganic compound.

With respect to the propargyl xanthate, this advantageously has the general formula (I):

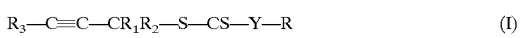

in which R is the residue of a primary, secondary or tertiary alcohol, optionally bearing other functional groups which may be protected, $R_1$, $R_2$ and $R_3$, which may be identical or different, are each a hydrogen atom or a linear or branched hydrocarbon radical having from 1 to 20 carbon atoms, advantageously from 1 to 10 carbon atoms, and Y is a chalcogen.

It is preferable that the sum of the carbon atoms in $R_1$, $R_2$ and $R_3$ be at most equal to 30.

The linear or branched hydrocarbon radicals having from 1 to 20 carbon atoms are here designated alkyl radicals (alkyl being used in an etymological sense of an alcohol residue after the alcohol function has been removed), including the aralkyl and aryl radicals. These hydrocarbon radicals may be substituted and may bear various free or protected functional groups.

In the above formulae, the radical R alkylates the nucleophile while at the same time, and where appropriate, undergoing Walden inversion (the radical having undergone Walden inversion will be designated R').

For such an inversion to be detected, R must not be primary.

Moreover, if it is desired to employ the process of invention to alkylate sterically hindered nucleophiles, it is preferable that R not be tertiary, or at least one of the subradicals borne by the carbon bearing the "free" valence bond should be methyl. Furthermore, certain of the tertiary alcohol xanthates are quite unstable and the risk is presented of conversion into alkenes more rapidly than alkylates.

Lastly, it should be appreciated that the present invention is especially useful for alkylating with relatively complex radicals, namely, radicals R in which the number of carbon atoms is at least equal to two, advantageously to three, and preferably up to 5 carbon atoms.

The subject process may, however, be advantageous for methylating, ethylating, propylating or butylating nucleophiles which are reputedly poorly nucleophilic (namely, those in which the nucleophilicity is less than that of the acetate, propionate or benzoate ions) or sterically hindered nucleophiles.

By the term "sterically hindered nucleophiles" are intended nucleophiles in which at least one of the atoms in an alpha, beta or gamma position to the prospective nucleophilic atom bearing the radical R, on the one hand includes at least two chains, and, on the other, does not contain a double bond. In the case of functions borne by aromatics, only rings in which at least one of the ortho positions is occupied will be considered to be sterically hindered.

Exemplary of the optionally protected primary, secondary or tertiary alcohol residues R are (1) those monocyclic or polycyclic hydrocarbons that are residues or derivatives of the steroid family such as, for example, cholesterol residues or derivatives thereof, cholestanol residues or derivatives thereof, optionally protected betulinic acid residues or derivatives thereof, and cholic acid residues or derivatives thereof; (2) the mono- or polycyclic heterocycles, including 5- to 7-membered monocyclic heterocycles such as pyrrolidine or derivatives thereof, piperidine or derivatives thereof, proline or derivatives thereof, thiazole or derivatives thereof, morpholine or derivatives thereof, quinuolidine, an optionally protected baccatin residue or derivatives thereof, and codeine or derivatives thereof; and (3) the optionally is mono- or polysubstituted, linear or branched alkyl radicals, including methyl, ethyl, propyl, i-propyl, n-butyl, i-butyl, pentyl, neopentyl, etc., radicals, with the proviso that these radicals may be substituted, in particular by one or more protected or unprotected amino or alkylamino radicals, or with a dialkylamino radical in which the alkyl moieties may optionally be substituted, or may together form a heterocycle which may comprise other hetero atoms selected from among nitrogen, oxygen and sulfur, or substituted by one or more alkyloxy or alkyloxycarbonyl radicals in which the alkyl moiety may optionally be substituted, or substituted by one or more protected carboxyl radicals, or substituted by one or more saturated, partially saturated or unsaturated mono- or polycyclic carbocyclic or heterocyclic radicals which may themselves be substituted.

Also exemplary are macrolide residues selected from among the synergistins of groups A and B such as, in particular, pristinamycins of type I and II, virginiamycins S, spiramycin, erythromycin and azithromycin.

Sugar residues are also exemplary, including nucleosides and nucleotides of an alkaloid, or of a steroid.

The radicals X are advantageously organic carboxylic acid residues, for example a saturated, partially saturated or unsaturated mono- or polycyclic radical which may optionally be substituted (with one or more optionally protected hydroxyl radicals, with alkyl, alkyloxy or alkylthio radicals, said alkyl, alkyloxy or alkylthio radicals themselves optionally being substituted (in particular by one or more halogen atoms or optionally protected hydroxyl radicals, optionally protected and optionally substituted amino radicals, aminocarbonyl and carboxamido radicals, protected carboxyl radicals, and alkyloxycarbonyl radicals, which may be heterocyclic, or saturated or unsaturated carbocycles which may themselves be substituted), or by one or more protected carbonyl radicals or alkyloxycarbonyl, methylene or oxo radicals), or a saturated, partially saturated or unsaturated mono- or polycyclic heterocyclic radical comprising one or more hetero atoms selected from among nitrogen, oxygen and sulfur and optionally substituted by radicals as described above in respect of the carbocyclic radicals, or an alkyl radical having from 1 to 10 carbon atoms, whether linear or branched, and optionally substituted by radicals as described above in respect of the carbocyclic radicals.

For example, the organic acid residue may, in particular, be a sugar residue in which the functions which may interfere with the reaction are protected beforehand, a nucleic acid residue in which the functions which may interfere with the reaction are protected beforehand, or an acid residue derived from a steroid compound.

Also exemplary are mono- or polycyclic heterocyclic radicals containing labile hydrogen atoms, such as, for example, a nitrogen-containing heterocyclic radical in which the moieties which may interfere with the reaction are protected beforehand, and which may comprise one or more other hetero atoms selected from among nitrogen, oxygen and sulfur.

Particularly exemplary are the radicals derived from a substituted tetrazolyl compound (for example phenyltetrazolyl) and from imidazolyl, triazolyl, phthalimido, 1-hydroxyphthalimido, 2-oxopyrrolidinyl, succinimido and isoxazolyl compounds.

The acids H—(X) are acids in the broad sense in which the pKa is in the range indicated below for acids promoting the conversion of propargyl xanthates into a species constituting an excellent leaving group, which conversion will permit the leaving group to form compounds of the 1,3-dithiol-2-one type (see "A novel synthesis of 1,3-dithiol-2-ones from S-propargyl dithiocarbonates" by Jean Boivin, Eric Henriet, Catherine Tailhan and Samir Z. Zard, *Tetrahedron Letters*, Vol. 34, pp. 2766–66 (1993)).

Among these acids, the acids comprising compounds having a hydrogen alpha to at least one electron-withdrawing function are exemplary. Electron-withdrawing functions including the sulfones, carbonyls, nitro groups, nitrites and equivalents thereof.

When the nucleophiles are not sufficiently acidic, a stronger acid (within the pKa limits indicated below) must be associated with the nucleophile in order to form the active species.

As indicated above, the present invention features a particular reactant which is useful for alkylating nucleophiles.

Such reactant is based on propargyl xanthate or on mesomeric compounds. It comprises, for successive or simultaneous addition:

(a) an alkyl propargyl xanthate; and (b) at least one Brönsted acid (or a source of H$^+$).

The latter component may constitute, with the nucleophilic substrate, a single compound which then possesses a weak or strong acid function.

The reactant advantageously contains a solvent. The solvents are preferably aprotic or sparingly protic and sparingly basic, in order to avoid interference with the acid and possibly the substrate.

The solvents are typically aromatic compounds or mixtures thereof. The solvent serves as a temperature regulator and is generally heated to boiling. The solvents are preferably inert in respect of the reactants and substrates used under the operating conditions of the invention.

The nucleophile may be neutral, including zwitterionic, or ionic. It bears at least one nucleophilic function or one nucleophilic atom. This function may be neutral or anionic.

The alkyl propargyl xanthate advantageously has the following formula (I):

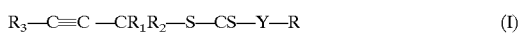

$$R_3{-}C{\equiv}C{-}CR_1R_2{-}S{-}CS{-}Y{-}R \qquad (I)$$

in which $R_1$, $R_2$ and $R_3$ are hydrocarbon radicals preferably having not more than 10 carbon atoms; R is an alkyl radical; and Y is a chalcogen.

The term alkyl is again used in an etymological sense to circumscribe any alcohol residue after the alcohol function has been removed.

The present invention is of special advantage for syntherisizng complex compounds, comprising radicals R in which the number of carbons is greater than one, more generally greater than two. Since the group derived from propargyl xanthate undergoes Walden inversion on leaving, the technique is particularly suitable for chiral syntheses and, in general, for any intricate synthesis.

The reaction according to the invention also presents the advantage of producing certain esters of esterification-resistant acids, for example acids which are sterically hindered alpha or beta to the carboxylic function.

In the present description the term "ester" is employed in its broadest sense, namely, a compound which is obtained by the condensation of an acid, even a non-oxygenated acid, with an alcohol and with removal of a water molecule comprising the alcohol function and the hydrogen of the acid.

By the term "acid" is intended a Brönsted acid or, in general, any compound which has at least one labile hydrogen atom, which is advantageously more acidic than water.

More specifically, its pKa advantageously is at most equal to 12, preferably at most 10.

Y is advantageously a light chalcogen; the second (sulfur) or preferably the first (oxygen) in the series are the chalcogens of choice.

It is preferred that the reaction be carried out under anhydrous conditions, i.e., the water content of the reaction medium is at most equal to 1%, advantageously not more than 0.1%, and preferably is about $10^{-4}$% (by weight).

The reaction temperature advantageously ranges from 50° to 200° C., preferably from 50° to 150° C. A solvent that refluxes at atmospheric pressure is generally employed.

The synthesis of xanthates is well known to this art and may be carried out by reacting an alkoxide with carbon disulfide, the salt obtained then being condensed with a halide or an optionally substituted propargyl pseudohalide.

The radical R corresponds to the radical derived from an alcohol or from a thioalcohol which is grafted onto the nucleophile.

In the present description, when the figure or figures on the extreme right of a number is or are zeros, these zeros are positional zeros and not significant figures, except, of course, if otherwise indicated.

The present invention also features a novel class of propargyl xanthates having the general formula (I):

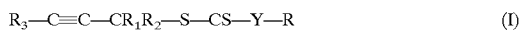

$$R_3\text{—}C\equiv C\text{—}CR_1R_2\text{—}S\text{—}CS\text{—}Y\text{—}R \qquad (I)$$

in which R and $R_1$, $R_2$ and $R_3$ are as defined above, with the proviso that, when $R_1$, $R_2$ and $R_3$ are all hydrogen and when Y is oxygen, R has at least 2 and preferably 3 carbon atoms.

In order to further illustrate the present invention and the advantages thereof, the following specific examples are given, it being understood that same are intended only as illustrative and in nowise limitative.

EXAMPLES

Starting Materials:

The alcohols used for the synthesis of the xanthates in the following examples are listed below:

| Alcohols | Reference | Source |
| --- | --- | --- |
| 1-Octyn-3-ol | 1-0 | commercially available |
| 1-Phenyl-1-butyn-3-ol | 2-0 | Luche method[1] |
| 1-Cyclohexene-1-butyn-3-ol | 3-0 | Luche method[1] |
| 1-Phenyl-1-propyn-3-ol | 4-0 | Luche method[1] |
| 4-Methyl-5-ene-2-hexyn-1-ol | 6-0 | commercially available |
| 1-Butyn-3-ol | 7-0 | commercially available |
| 2-Methyl-3-butyn-1-ol | 13-0 | commercially available |
| 1-Triphenylmethoxy-2-propanol | 14-0 | see below |
| Diacetone glucose | 15-0 | commercially available |
| Benzyl alcohol | 16-0 | commercially available |
| 3-Methyl-3-oxatanemethanol | 17-0 | commercially available |
| Codeine | 18-0 | commercially available |
| S-(+)-3-Quinuclidinol | 19-0 | commercially available |
| 3-Quinuclidinol | 19-0 | commercially available (racemic mixture) |
| 1-Cyclohexene-1-propyn-3-ol | 23-0 | Luche method[1] |
| 1-Phenyl-2-propyn-1-ol | 24-0 | commercially available |
| (+/−)-Menthol | 25-0 | commercially available |
| 2-Octanol | 26-0 | commercially available |
| Phenethyl alcohol | 27-0 | commercially available |

[1]Denis, Green, Serra & Luche, J. Org. Chem., 51, 46 (1986).

The first figure of the reference employed herein is utilized in the following examples to indicate the presence of the radical derived from these alcohols.

I. Preparation of 1-triphenylmethoxy-2-propanol (14-0):

To prepare 1-trityloxy-2-propanol 14-0, a method from the literature was employed (Haubrandt, Osterman-Golkar Wachtmeister, Acta Chem. Scand., 23, No. 3 (1968)).

25 g of trityl chloride (MW=278.5) and 6.75 g of 1,2-propanediol (MW=76) in 75 ml of pyridine were introduced into a round-bottomed flask.

The trityl chloride was purified beforehand by recrystallization from 5 volumes of petroleum ether per one volume of acetyl chloride, using 1.8 g of this solvent per 1 g of trityl chloride, and by drying in a desiccator (Org. Synth Col., Volume III (1955)).

The mixture was maintained for 48 hours at 20° C.

It was then poured into 200 ml of chloroform and extracted with 4M hydrochloric acid (200 ml).

The extracts were washed with water and then with saturated 1M $NaHCO_3$ solution, followed by drying with sodium sulfate.

The product was recrystallized from cyclohexane (one month).

The desired alcohol was obtained (16.2 g, MW=318.4) in a yield of 57%.

II. Preparation of the S-alkyl xanthates RSCSOR':

II-1 By displacement of the corresponding mesylates with the xanthate salt:

II-1.1 Preparation of the mesylates:

Y mmol (1.0 to 1.1 eq) of triethylamine was added to X mmol of alcohol in V ml of dry ether, in a three-necked flask fitted with an inlet and an outlet for inert gas (nitrogen or argon). The mixture, maintained under magnetic stirring and under an inert atmosphere, was cooled in an ice bath. Z mmol (1.1 to 1.5 eq) of mesyl chloride dissolved in a few milliliters of dry ether was introduced dropwise into the above solution. The reaction was readily controllable by precipitation of the salt of the base formed. This salt was then filtered off on a Buchner funnel and washed with the solvent used to entrain all of the mesylate formed. Washing was carried out with saturated $NaHCO_3$ solution, followed by extraction with ether. The filtrate was then evaporated. The product obtained was used crude in the following step. The following results were obtained (N.B.: since the mesyl chloride used was not pure, the number of equivalents used had to be increased in certain instances).

TABLE 1

| ALCOHOLS | 1-0 | 2-0 | 3-0 | 4-0* | 6-0 | 7-0 | 23-0 |
| --- | --- | --- | --- | --- | --- | --- | --- |
| X mmol | 46 | 25 | 20 | 45 | 41 | 140 | 7.35 |
| Triethylamine, Y mmol | 220 | 252 | 198 | 53 | 220 | 387 | 8.3 |
| Dry ether, V ml | 200 | 150 | 180 | 200 | 200 | 100 | 25 |
| MaCl, Z mmol | 188 | 150 | 120 | 47 | 188 | 357 | 16.7 |
| Mesylate obtained | 1-1 | 2-1 | 3-1 | 4-1 | 6-1 | 7-1 | 23-1 |

II-1.2 Preparation of xanthates from the mesylates:

To Y mmol (1.0 to 1.5 eq) of an alcohol, xanthate salt dissolved in:

(i) methanol for —R'=-methyl, (ii) ethanol for —R'=-ethyl (except for 23-1 where acetone was used), was added dropwise, at room temperature and with magnetic stirring throughout, X mmol (1.0 eq) of mesylate.

Very rapid formation of a precipitate of potassium chloride was observed.

The reaction mixture was then poured into water and was extracted with a petroleum ether/ether mixture (70/30). The organic phase was then dried over sodium sulfate, filtered and evaporated.

The xanthate thus obtained was used crude in the following synthesis.

The following results were obtained:

TABLE 2

| MESYLATES | 1-1 | 2-1 | 3-1 | 4-1 | 6-1 | 7-1 | 7-1 | 23-1 |
|---|---|---|---|---|---|---|---|---|
| X mmol | 44 | 25 | 20 | 19 | 14 | 143 | 143 | 7.35 |
| EtOSCS⁻ K⁺, mmol | 50 | 37.5 | 30 | 29* | 21 | 143 | 143* | 11 |
| Absolute EtOH or MeOH | 135 | 100 | 100** | 50* | 135 | 120 | 120* | 50*** |
| Yield % | 70 | 67 | 65** | 86.5 | 72 | 81 | 70 | >95 |
| Ref. of the Xanthates obtained | 1-2 | 2-2 | 3-2 | 4-2* | 6-2 | 7-2 | 8-2* | 23-2 |

*These were methyl xanthates.
**For the example beginning with mesylate 31, two tests were carried out with two different solvents: ethanol and acetone. The reason for this is that is appeared that with ethanol, addition products of the latter with the allene were also obtained, the rearrangement working even at low temperature. The results reported in Table 2 were those relating to the test in ethanol.
***The solvent used was acetone.

II-2 Method using n-butyllithium:

II-2.1 Preparation of propargyl cholesteryl dithiocarbonate:

2.84 mmol of cholesterol (1.1 g, MW=386.66) in 50 ml of dry THF were introduced into a three-necked flask with an argon inlet and a dropping funnel. A few crystals of 2,2'-bipyridine were added thereto. 2.5 M n-butyllithium in hexane was added until a red color persisted (2.84 mmol, MW=64.06, d=0.88, V=2.5 ml). The mixture was maintained stirred and 13 mmol of $CS_2$ (1 g, 0.8 ml) were then added. The mixture was stirred at room temperature for 20 minutes. 15 mmol of propargyl chloride (1.123 g, 5 eq, M=74.51) were then added. The reaction was monitored by TLC. The reaction mixture was extracted with dichloromethane and brine. The organic extracts were dried with $Na_2SO_4$ and the dichloromethane was evaporated off.

After column chromatography (eluent: petroleum ether) cholesteryl xanthate was recovered. The yield was about 80% with respect to xanthate and allene.

II-2.2 Preparation of propargyl cholestanyl dithiocarbonate 12-0:

7.72 mmol of cholestanol (3 g, MW=388.66) in 50 ml of dry THF were introduced into a three-necked flask with an argon inlet and a dropping funnel.

A few crystals of 2,2'-bipyridine were added thereto.

2.5 M n-butyllithium in hexane was added until a red color persisted (MW=64.06, d=0.88, V=3 ml).

The mixture was maintained stirred and 54 mmol of $CS_2$ (7 eq, 4.1 g, 3.3 ml, MW=76) were then added.

The mixture was stirred at room temperature for 20 minutes.

38.6 mmol of propargyl chloride (2.9 g, 5 eq, M=74.51) were then added. The reaction was monitored by TLC (thin layer chromatography).

The reaction mixture was extracted with dichloromethane and brine.

It was dried with $Na_2SO_4$ and the dichloromethane was evaporated off.

After column chromatography (eluent: petroleum ether) cholestanyl xanthate was recovered. The yield with respect to xanthate and allene was quantitative.

II-3 Method using Potassium hydride KH:

A suspension of potassium hydride in oil was introduced into a three-necked flask (which had been calibrated) under argon.

Dry pentane was added; the mixture was stirred for one minute and the pentane supernatant was pipetted off.

This process was repeated three times, thereby washing the oil from the hydride.

The hydride was then dried under a strong stream of argon.

A dry hydride powder was thus obtained.

The flask was weighed and the amount X of KH (MW=40.11) placed therein was determined therefrom.

V ml of dry THF was then added and the mixture was heated to 78° C.

Y mmol of alcohol were then added using a dropping funnel.

The reaction progress was monitored by measuring the hydrogen released. When there was no further release of hydrogen, the temperature was decreased to 0° C. and 2 to 3 eq of $CS_2$ (V' ml, MW=76) were added.

The temperature was then permitted to return to room temperature, over thirty minutes.

W g of propargyl chloride (MW=74.51, 3 to 4 eq) were then added.

The mixture was poured (except in the special case) into aqueous citric acid solution.

This mixture was extracted with ether and dried with sodium sulfate. After rapid column chromatography, the desired propargyl xanthate was recovered.

The following results were obtained:

TABLE 3

| XANTHATES | 14-1 | 15-1 | 17-1 | 18-1 | 19-1r | 19-1s | 25-1 | 26-1 | 27- |
|---|---|---|---|---|---|---|---|---|---|
| KH, X mmol | 56.3 | 47.1 | 82.0 | 3.73 | 6.73 | 13.1 | 24.9 | 35.6 | 39.0 |
| Dry THF, V ml | 20 | 20 | x | 5 | 5 | 10 | 15 | 20 | 30 |
| Alcohol, Y mmol | 56.3 | 47.1 | 90 | 3.4 | 7 | 13.1 | 26.2 | 37.4 | 42.5 |
| $CS_2$, V' ml | 5 | 5.7 | 25 | 0.7 | 1.3 | 2.5 | 4.5 | 6.5 | 7.0 |

TABLE 3-continued

| XANTHATES | 14-1 | 15-1 | 17-1 | 18-1 | 19-1r | 19-1s | 25-1 | 26-1 | 27- |
|---|---|---|---|---|---|---|---|---|---|
| Prop. chlor., W g | 7.5 | 7.5 | 15.2 | 0.9 | 1.0 | 2 | 3.8 | 5.3 | 5.9 |
| Yield, % | 92 | 96 | 2.6 | 23.9 | 90 | 88 | 62 | >95 | >95 |

*In this experiment, the solvent used was the $CS_2$ itself. The low yield is likely explained by the high volatility of the product. It was necessary to simultaneously distil off the $CS_2$ and the extraction ether, using a cardice trap.

IV. Preparation of Simple Esters:

IV-1 Thermal reaction of the corresponding acid with an S-propargyl xanthate:

The S-propargyl xanthate used was S-(1-butyn-3-yl) O-ethyl dithiocarbonate, 7-2, S-(1-butyn-3-yl) O-methyl dithiocarbonate 8-2 or S-(1-propyn-3-yl) O-neopentyl dithiocarbonate 10-0.

A solution of X mmol of xanthate and Y mmol of acid in V ml of chlorobenzene or toluene, depending on the particular case, was heated at reflux for approximately 5 hours.

The reaction was monitored by TLC (thin layer chromatography).

The solvent was evaporated off (in the case of toluene) on a rotary evaporator. In certain instances, the ester crystallized at this stage; this ester was then filtered off and recrystallized. Otherwise, column chromatography was carried out (the product was thus freed of the solvent in the case of chlorobenzene) and the ester was recrystallized.

The operating conditions are indicated in Table 4 below. In addition to the ester, a mixture of the two isomers of the 1,3-dithiol-2-one corresponding to the xanthate used was obtained in each experiment.

TABLE 4

| ESTER | X, mmol | Y, mmol | V, ml | Time |
|---|---|---|---|---|
| 7A | 4.4 | 4.4 | 6 | 5 h |
| 7B | 0.23 | 0.23 | 5 | 1.5 h |
| 8A | 0.393 | 0.393 | 4 | 5 h |
| 8B | 0.325 | 0.6 | 4 | 5 h |
| 8C | 0.325 | 0.6 | 4 | 4 h |
| 8D | 0.365 | 0.6 | 4 | 5 h |
| 8F | 0.365 | 0.6 | 4 | 5 h |
| 8G | 0.466 | 0.7 | 5 | 5 h |
| 8H | 1.02 | 1.53 | 5 | 4 h |
| 8I | 1.3 | 1.95 | 4 | 5 h |
| 8J | 1.3 | 1.95 | 5 | 5 h |
| 10A | 0.92 | 1.38 | 4 | 5 h |

The following results were obtained:

TABLE 5

| ACID | ESTER Ref. | ESTER TYPE | SOLVENT | Yield % | Encrypt. |
|---|---|---|---|---|---|
| Triphenylacetic | 7A | Ethyl | PhCl | 74 | V.2 |
| 3-Acetoxy-11-ketocholanic | 7B | Ethyl | PhCl | 87 | $CHCl_3$ |
| 3-Acetoxy-11-ketocholanic | 8A | Methyl | Toluene | 94 | $CHCl_3$ |
| 18-beta-Glycyrrhetinic | 8B | Methyl | Toluene | 98.5 | EtOH |
| Gibberellic | 8C | Methyl | Toluene | 78.4 | AcOEt |
| Podocarpic | 8D | Methyl | Toluene | 95.2 | EtOH |
| Hederagenin | 8F | Methyl | PhCl | 51.3 | MeOH |
| Uracyl sugar | 8G | Methyl | Toluene | 91 | $CHCl_3$ |
| Sugar | 8H | Methyl | Toluene | 95.7 | Hexane |
| Coumalic | 8I | Methyl | Toluene | 92 | $CHCl_3$ |
| N-acetyltryptophan | 8J | Methyl | Toluene | 81.5 | AcOEt |
| Sugar | 10A | Neopentyl | Toluene | 93 | |

V. Preparation of More Complex Esters:

V-1 Cholesteryl benzoates:

1.1 mmol of xanthate (propargyl cholesteryl dithiocarbonate) (0.547 g, MW=500.66) and 1.5 eq of benzoic acid (1.65 mmol, 0.2 g, M=122) were maintained at reflux in toluene (5 ml) for 5 hours. After evaporation of the solvent, column chromatography was carried out to recover the 3β-benzoate 11A and the 5β-benzoate 11A' resulting from the i-steroid phenomenon. The overall yield was 65%. The 1,3-dithiol-2-ones 10-3 and 10-4 were obtained as byproduct, along with a trace amount of 2-cholestene.

V-2 Cholestanol esters:

V-2.1 Procedure:

X mmol of cholestanyl xanthate 12-0 (MW=502.68) and Y mmol of acid in V ml of toluene were introduced into a round-bottomed flask.

The mixture was maintained at reflux for approximately 5 hours.

The solvent was evaporated off and the mixture was dried under nitrogen and chromatographed on a column to recover the ester.

The following results were obtained:

TABLE 6

| Acid | Ester | X, mmol | Y, mmol | V, ml | Yield, % |
|---|---|---|---|---|---|
| Benzoic | 12A | 0.628 | 1.2 | 4 | 65.75 |
| Benzoic | 12A bis | 0.302 | 0.6 | 4 | 70.6 |
| Galacturonic | 12B | 0.24 | 0.18 | 4 | 97 |
| Coumalic | 12I | 0.503 | 0.553 | 4 | 77.1 |
| Thiobenzoic* | 12J | 0.491 | 0.54 | 5 | 50 |

*For all of these experiments, the complementary yield comprised 2-cholestene, except in the case of thiobenzoic acid, where 24% of 2-cholestene (fraction 1) was obtained. The presence of a cholestene (MW = 370) which may be 3-cholestene was also noted in fraction 2.

V-5 Ester from 3-methyl-3-oxetanemethanol:

2.0 mmol of xanthate 17-1 (MW=216) and 2.0 mmol of N-acetyltryptophan in 3 ml of toluene were introduced into a round-bottomed flask.

The mixture was maintained at reflux for approximately 5 hours.

The solvent was evaporated off and the product was dried under nitrogen and chromatographed on a column to recover the ester.

It was obtained in a yield of 79%.

V-6 Codeine benzoate:

0.237 mmol of xanthate 18-1 (MW=413) and 0.300 mmol of benzoic acid in 2.5 ml of toluene were introduced into a round-bottomed flask.

The mixture was maintained at reflux for approximately 5 hours.

The solvent was evaporated off and the mixture was basified and extracted with a dichloromethane/petroleum ether mixture (50/50). The product was dried with sodium sulfate and chromatographed on a column to recover the ester, in a yield which remained to be determined.

V-7 3-Quinuclidinyl benzoates:

V-7.1 Starting with a racemic mixture of 3-quinuclidinol:

3.45 mmol of the racemic mixture of xanthate 19-1 (MW=240) and 6.9 mmol of benzoic acid in 4 ml of toluene were introduced into a round-bottomed flask.

The mixture was maintained at reflux for approximately 5 hours. The solvent was evaporated off and the residue was washed with saturated $NaHCO_3$ solution and extracted with ether.

The product was dried over sodium sulfate and chromatographed on a column to recover the ester (eluent: ether/dichloromethane/triethylamine=45/50/5). The yield was 63%.

The mixture of the 1,3-dithiol-2-ones was also recovered as the first column fraction.

In order to verify inversion, a control was prepared (non-inverted benzoate) by placing 50 mg of S-(+)-quinuclidinol in 2 ml of pyridine and adding 0.1 ml of PhCOCl (MW=140.5, d=1.211). After one week, the mixture was poured into $NaHCO_3$ and extracted with ether.

V-8 (±)-Menthyl benzoate:

1.85 mmol of xanthate 25-1 (MW=270) and 1.48 mmol of benzoic acid in 3.5 ml of toluene were introduced into a round-bottomed flask.

The mixture was maintained at reflux for approximately 6 hours. The solvent was evaporated off and the residue was dried under nitrogen and chromatographed on a column to recover the ester. The yield was 47%.

10% of starting xanthate and the mixture of the 1,3-dithiol-2-ones were also recovered.

The two starting menthol isomers were in equatorial/axial proportions=3/2 (determined by $^1H$ NMR). These proportions were conserved during preparation of the xanthate.

On the other hand, inversion of this ratio may be observed in the proton spectrum of the benzoate. By hydrolyzing the mixture of the two benzoates (e/a=2/3), menthol was recovered in inverted proportions relative to that used at the start.

VI. Related Reactions:

VI-1 Preparation of phosphates and phosphites:

X mmol of xanthate and Y mmol of diphenyl phosphate (MW=250.19) or dimethyl phosphite (MW=110.05, d=1.2) in V ml of toluene were introduced into a round-bottomed flask fitted with a reflux condenser and a stirrer.

The mixture was heated to reflux. After processing (column chromatography), the following results were obtained:

TABLE 7

| Reactant | Xanth. | X | Y | V | Yield | Cholestene |
|---|---|---|---|---|---|---|
| Phosphate | 12-0 | 0.56 | 0.62 | 4 | 28.00% | 68.90% |
| Phosphate | 26-0 | 1.86 | 3.19 | 3.5 | 18.00% | |
| Phosphite | 12-0 | 0.36 | 0.65 | 3 | 27.30% | 58.30% |

VI-2 Preparation of cholestane halides:

X mmol of cholestanyl xanthate 12-0 (MW=502.68) and Y mmol of 4-chloropyridine HCl (for the chloro compound), triethylamine trihydrofluoride (for the fluoro compound) or $Et_3N.HI$ for the iodo compound) in 3 to 4 ml of toluene were introduced into a round-bottomed flask fitted with a reflux condenser and a stirrer. The mixture was heated to reflux.

After processing (column chromatography), the following results were obtained:

TABLE 8

| Reactant | Product | X, mmol | Y, mmol | 2-Cholestene | Halid |
|---|---|---|---|---|---|
| "HCl" | 12G | 0.157 | 0.345 | 14.13% | 59.20% |
| "HF" | 12H | 0.219 | 0.438 | 38.20% | 60.35% |
| "HI" | 12L | 0.53 | 1.6 | 3.50% | 58.4% |

*In the case of the iodination, the yields were:
iodide: 58.4% (fractions 1 and 2)
2-cholestene (by $^2H$ NMR): 3.50% (fraction 1)
xanthate 12-0: 35.16%
cholestanol: 3.30%

Preparation of $Et_3N.HI$:

0.104 mol of 67% HI (20 g) was added dropwise to a round-bottomed flask containing 0.31 mol of triethylamine (50 ml). The mixture was filtered and the reactant was recovered quantitatively.

VII. Various Methylations:

VII-1 Methylation of tetrazoles with 8-2:

0.64 mmol of phenyltetrazole (0.0935 g, MW=146; pKa=4.4) and 1 mmol of xanthate 8-2 (0.16 g, MW=160) were introduced into a round-bottomed flask containing 4 ml of toluene. The mixture was maintained at reflux for 5 hours and the toluene was evaporated off. 0.097 g of a mixture of the methylated isomers at 2 and 3=1/7.25, equivalent to a yield of 95.0, was collected.

VII-2 Methylation of N-hydroxyphthalimide with 8-2:

0.83 mmol of N-hydroxyphthalimide (0.135 g, MW=163.13) and 1.5 eq (1.245 mmol, 0.2 g, MW=160) of xanthate 8-2 were introduced into a round-bottomed flask containing 4 ml of toluene, a stirrer and a reflux condenser. The mixture was maintained at reflux for 5 hours and the solvent was evaporated off.

After chromatography on a small column, 0.0752 g of the product 9C, equivalent to a yield of 52%, was collected.

VII-3 Methylation of isoxazolones with 802:

0.63 mmol of benzylisoxazolone (0.158 g, MW=251) and 0.63 mmol of xanthate 8-2 (0.1 g, MW=160) were introduced into a round-bottomed flask containing 4 ml of toluene. The mixture was maintained at reflux for 5 hours and the toluene was evaporated off. The product was then chromatographed on a column of silica.

A mixture of methylated isoxazolones 9E was recovered in a yield of 56.4%, together with the 1,3-dithiol-2-ones.

VII-4 Methylation of saccharin with 8-2:

6.7 mmol of saccharin (MW=183.19) and 7 mmol of xanthate 8-2 (MW=160) were introduced into a round-bottomed flask containing 8 ml of toluene. The mixture was maintained at reflux for 5 hours. The crystals were separated from the residue with petroleum ether and were then washed with dichloromethane. They were recrystallized from boiling water. Sublimation of the crystals beginning at 129° C. was verified.

The methylated saccharin 9F was obtained in a yield of greater than 90%, together with the 1,3-dithiol-2-ones.

VII-5 Methylation of triazoles with 8-2:

10.1 mmol of 1,2,4-triazole (MW=69) and 13.2 mmol of xanthate 8-2 (2 g, MW=160) were introduced into a round-bottomed flask containing 3 ml of toluene. The mixture was maintained at reflux for 5 hours and the toluene was evaporated off.

After processing (column), two fractions (Nos. 5 and 6) were collected, the characteristics of which are reported below and which fractions, in accordance with the literature, appeared to contain methylated triazoles. Fraction 6 weighed 0.21 g (i.e., 25.1% if it were the expected product.

VIII. Alkylation of Inidazole with S-propargyl O-octyl Dithiocarbonate:

8.4 mmol of imidazole (0.57 g, MW=68.08, 1.2 eq; pKa=14) and 1.4 mmol of camphorsulfonic acid monohydrate (0.34 g, MW=250.32, 0.2 eq) were introduced into a round-bottomed flask containing 8 ml of toluene.

The toluene was evaporated off by boiling until 4 ml remained. The reaction medium was thus dehydrated by azeotropy.

0.7 mmol of triethylamine (0.07 g, MW=101.1 g, 0.1 eq) and 7 mmol of octyl xanthate 26-1 (1.65 g, MW=236.1 eq) were then added. The mixture was maintained at reflux of the toluene for 5 hours. The toluene was evaporated off and rapid chromatography on a column of silica was carried out.

The following yields were obtained:

(a) 13.8% of N-octyloxycarbonylimidazole, (b) 25.5% of N-(2-octyl)imidazole.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A propargyl xanthate having the formula (I):

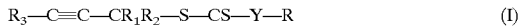

(I)

in which R is the residue of a primary, secondary or tertiary alcohol after the alcohol function has been removed; $R_1$, $R_2$ and $R_3$, which may be identical or different, are each a hydrogen atom, or a linear or branched hydrocarbon radical having from 1 to 20 carbon atoms; and Y is a chalcogen; with the proviso that, when $R_1$, $R_2$ and $R_3$ are each hydrogen and Y is oxygen, R has at least 2 carbon atoms.

2. A propargyl xanthate having the formula (I):

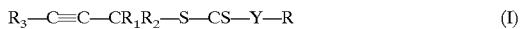

(I)

in which R is an alkyl radical; $R_1$, $R_2$ and $R_3$, which may be identical or different, are each a hydrogen atom, or a linear or branched hydrocarbon radical having from 1 to 20 carbon atoms; and Y is a chalcogen; with the proviso that, when $R_1$, $R_2$ and $R_3$ are each hydrogen and Y is oxygen, R has at least 2 carbon atoms.

* * * * *